United States Patent [19]

Mault

[11] Patent Number: 4,917,108

[45] Date of Patent: Apr. 17, 1990

[54] OXYGEN CONSUMPTION METER

[76] Inventor: James R. Mault, 2621 W. Cornwallis, Durham, N.C. 27705

[21] Appl. No.: 213,184

[22] Filed: Jun. 29, 1988

[51] Int. Cl.$^4$ .............................................. A61B 5/08
[52] U.S. Cl. .................................. 128/718; 128/719; 128/725; 374/31
[58] Field of Search .................. 374/39, 102; 128/719, 128/730, 718

[56] References Cited

U.S. PATENT DOCUMENTS

| | | |
|---|---|---|
| 2,838,399 | 6/1958 | Vogel, Jr. . |
| 2,920,012 | 1/1960 | Sanders et al. ........................ 167/51.5 |
| 3,213,684 | 10/1965 | Seaton et al. ............................ 73/190 |
| 3,250,270 | 5/1966 | Bloom . |
| 3,523,529 | 8/1970 | Kissen . |
| 3,681,197 | 8/1972 | Smith ........................................ 195/63 |
| 3,726,270 | 4/1973 | Griffis et al. ............................ 128/719 |
| 3,814,091 | 6/1974 | Henkin . |
| 3,834,375 | 9/1974 | Sanctuary et al. ..................... 128/719 |
| 3,938,551 | 2/1976 | Henkin .................................... 137/613 |
| 4,051,847 | 10/1977 | Henkin . |
| 4,186,735 | 2/1980 | Henneman et al. . |
| 4,188,946 | 2/1980 | Watson et al. . |
| 4,211,239 | 7/1980 | Raemer et al. ........................ 128/716 |
| 4,221,224 | 9/1980 | Clark ...................................... 128/718 |
| 4,341,867 | 7/1982 | Johansen .............................. 435/189 |
| 4,368,740 | 1/1983 | Binder .................................... 128/718 |
| 4,386,604 | 7/1983 | Hershey ................................. 128/718 |
| 4,572,208 | 2/1986 | Cutler et al. ........................... 128/718 |
| 4,598,700 | 7/1986 | Tamm .................................... 128/671 |
| 4,619,269 | 10/1986 | Cutler et al. ........................... 128/719 |
| 4,753,245 | 6/1988 | Gedeon ............................. 128/719 X |
| 4,756,670 | 7/1988 | Arai ................................... 128/719 X |

OTHER PUBLICATIONS

"Caloric Requirements in Total Parenteral Nutrition" Foster et al., from Journal of the American College of Nutrition, vol. 6, No. 3, 231–253 (1987).

Primary Examiner—Daniel M. Yasich
Attorney, Agent, or Firm—Krass & Young

[57] ABSTRACT

An indirect calorimeter for calculating the metabolic rate of a subject by measuring the oxygen consumption during respiration over a period of time includes a gas flow meter providing output electric signals to a microprocessor which drives a display and printer. A carbon dioxide scrubber is connected to the flow meter and a respiratory connector including a mouthpiece so that inhaled gas passes first through the scrubber and then through the flow meter before being provided to the subject's respiratory system through the mouthpiece. The exhaled gas passes through the scrubber and then through the flow meter. The difference in volume between the inhaled gas and the exhaled gas is proportional to the oxygen consumption of the subject and the microprocessor integrates that signal over the time of the test, and multiplies it by a constant to provide a metabolic rate display. By passing both the inhaled and exhaled gases through the scrubber before their volume is measured, their temperature and humidity are modified to a state of equal temperature and humidity.

10 Claims, 2 Drawing Sheets

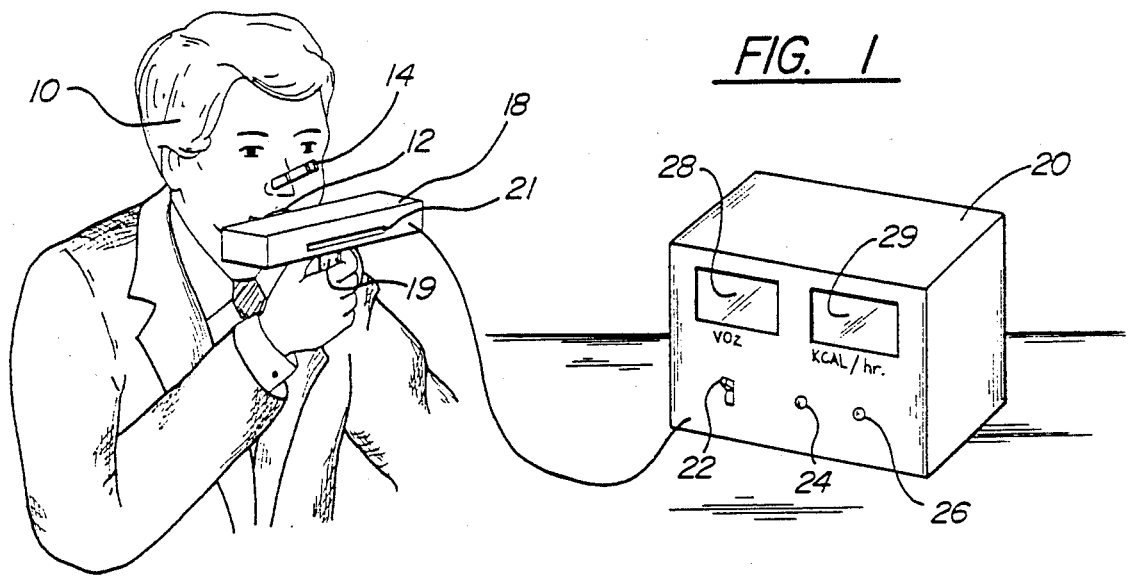
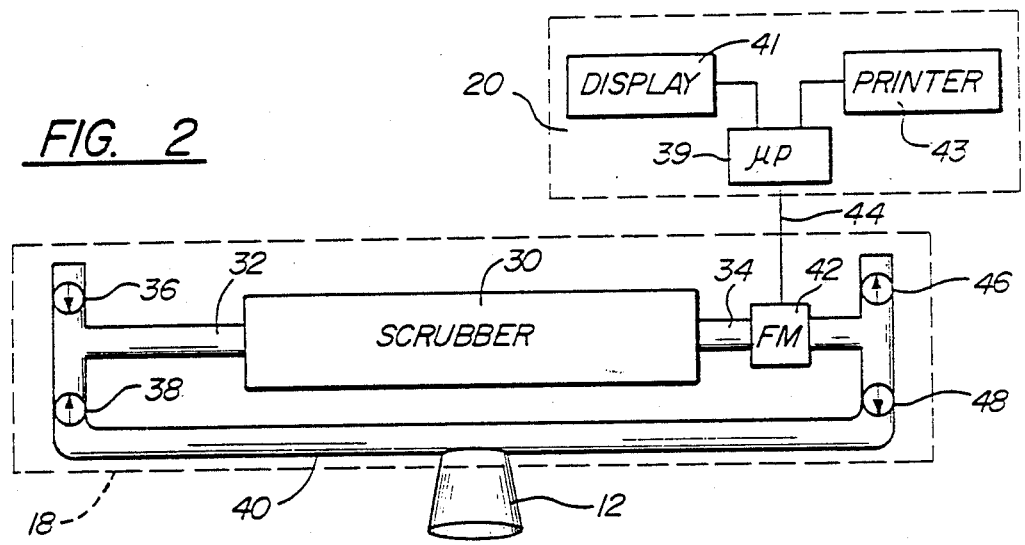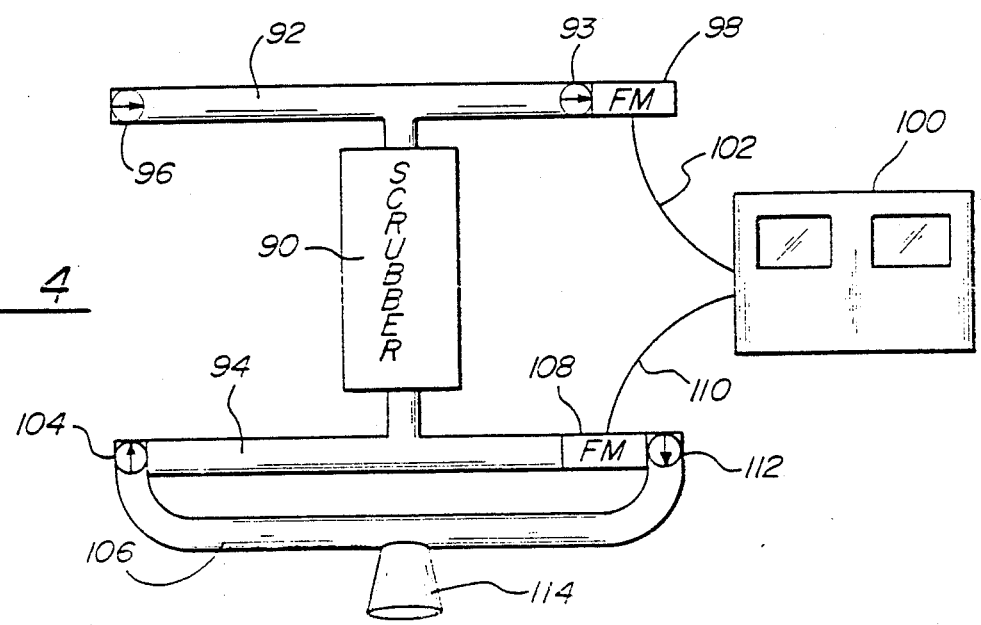

OXYGEN CONSUMPTION METER

FIELD OF THE INVENTION

This invention relates to indirect calorimeters for measuring metabolic rate on the basis of respiratory oxygen consumption and more particularly to such a calorimeter which scrubs the $CO_2$ from the exhaled gas and computes the difference between the inhaled gas volume and the volume of the scrubbed exhaled gas to calculate oxygen consumption.

BACKGROUND OF THE INVENTION

Measurement of the energy expenditure of humans is important for a number of reasons. For nutritional purposes measurement of the resting energy expenditure is important to a determination of the proper caloric content for feedings of hospitalized patients in view of the fact that certain diseases and traumas may cause the resting energy expenditure to vary substantially from normal values. In burn patients the metabolic rate may increase by as much as 300%. Other hospital situations in which the measurement of rate of metabolic oxygen consumption is important include the adjustment of parental feedings for infants, and the control of respiratory gases during surgical operations.

The resting energy expenditure may also decrease substantially in the course of a weight loss diet, and knowledge of this basal energy requirement is important to the adjustment of caloric inputs in order to achieve a target loss. Similarly, knowledge of caloric consumption during exercise is useful for cardiac rehabilitation and athletic training.

A variety of indirect calorimeters for measuring oxygen consumption during respiration have been devised and are available commercially. These broadly include closed circuit devices wherein oxygen depleted during respiration is replenished from an oxygen source and the volume of replenishing oxygen is measured to determine respiratory oxygen consumption. A device of this type is manufactured by ICOR AB, Bromma, Sweden. Open circuit devices generally measure the volume of inhaled gas and the proportions of carbon dioxide and oxygen in exhaled gas to determine the respiratory oxygen consumption. Devices of this class are disclosed in U.S. Pat. Nos. 3,523,529, 4,619,269, 4,221,224 and 4,572,208.

All of these devices are relatively complex and expensive and require specially trained technicians for their operation. Their use has largely been limited to hospital settings for the adjustment of nutritional requirements for critically ill patients in intensive care units.

A potentially simpler and less expensive form of calorimeter would measure the inhaled gas volume, pass the exhaled gas over a carbon dioxide scrubber to remove the lung contributed $CO_2$ from the exhaled gas and then measure the remaining gas volume. The difference between the two measured volumes would be a direct function of the respiratory oxygen consumption. However, because the exhaled gas has substantially different temperature and water vapor content than the inhaled gas, the volume measurements may grossly misestimate the actual oxygen consumption. Additionally, because such a device would measure variations in the relatively small differential between two large measurements, design of the device to attain a reasonable accuracy presents a problem.

SUMMARY OF THE INVENTION

The present invention is accordingly directed toward a simple and low cost indirect calorimeter or oxygen consumption meter that overcomes the deficiencies of the prior art and may be used by relatively untrained personnel so that it is adapted to use in a wide variety of situations for measurement of oxygen consumption and energy expenditure. The calorimeter of the present invention can operate from atmospheric air or any other oxygen source and utilizes a chemical carbon dioxide scrubber, and inhaled and exhaled air volume flow meter means. The scrubber, the flow meter, an inhaled air source and a mouthpiece are interconnected with conduits and one-way valves so that inhaled air passes through the scrubber before its volume is measured and is then passed to the mouthpiece, and exhaled air similarly passes through the scrubber before its volume is measured.

As the exhaled air passes through the scrubber, the chemical reaction between carbon dioxide and the absorber substance ($CO_2 + NaOH = \Delta + H_2O + Salt$) raises the temperature and water vapor content of the scrubber. Using one way valves, the inhaled and exhaled breaths are directed through the scrubber before their respective volumes are measured. After a short period of operation the inhaled and exhaled air will have substantially the same temperature and water vapor content so that their volumes, as measured by the flow sensor, may be directly compared without the need for temperature/water vapor measurement adjustment.

The flow meter means preferably provides pulsed signals with each electric pulse representing an increment of flow volume, and the system includes a microprocessor-based computation and display unit which receives the pulse signals, distinguishes inhalations from exhalations, and generates integrals of their differences over a period of time. The microprocessor preferably stores these integrated different signals for short periods of time representing increments of use of the calorimeter during the test and at the conclusion of the test displays the value representing the oxygen consumption over the latter portion of the test, multiplied by a constant to arrive at the display of kilocalories per 24 hour time. This arrangement discards the initial readings which may be inaccurate until the scrubber chemicals have built up a stable temperature and water vapor level. The integration of a large number of respiration cycles minimizes error resulting from limited repeatability of the flow sensor.

A preferred embodiment of the invention, which will subsequently disclosed in detail, employs a single flow meter for measuring both the inhaled and exhaled volume, thereby eliminating a possible differential of accuracy between separate meters as an error source. The flow meter, which is of the turbine type, is connected to receive the output of the scrubber. Conduits and one-way valves connect the mouthpiece to both the inlet of the scrubber and the output of the flow meter. When the user inhales, atmospheric air is drawn into the scrubber, through the flow meter, to the mouthpiece. Exhaled air passes through the scrubber and the flow meter to the atmosphere. The microprocessor analyzes the train of pulses it receives from the flow meter to distinguish inhalations from exhalations based on the integrated volume of each breath since the exhaled air will have a lower volume than the inhaled air since it loses more carbon dioxide to the scrubber. In an alternative embodiment, the system includes a flow direction sensor disposed in one of the conduits and connected to the microprocessor so that the microprocessor can distinguish inhalations and exhalations from the flow direction of the air that passes over the direction sensor.

The present calorimeter may also be used in positive pressure ventilation systems using any concentration of oxygen source. This included intensive care mechanical ventilators and closed loop anesthesia. The present invention may also be applied to exercise stress testing.

In an alternative embodiment of the invention separate flow sensors may be provided for the inhaled and exhaled volume, eliminating the need for the microprocessor to distinguish pulse trains associated with the inhaled and exhaled breaths.

The device of the present invention is thus simple, inexpensive, easy to use, and has excellent accuracy.

BRIEF DESCRIPTION OF THE DRAWINGS

Other objectives, advantages, and applications of the present invention will be made apparent by the following detailed description of a preferred embodiment of the invention. The description makes reference to the accompanying drawings in which:

FIG. 1 is a perspective view of the preferred embodiment of the indirect respiratory calorimeter of the present invention being used by a subject;

FIG. 2 is a schematic illustration of the gas flow circuitry of the embodiment of FIG. 1;

FIG. 4 is a schematic illustration of an alternative embodiment of the invention employing separate flow sensors for inhaled and exhaled gas.

DETAILED DESCRIPTION OF THE PREFERRED EMBODIMENT

Figure 3:
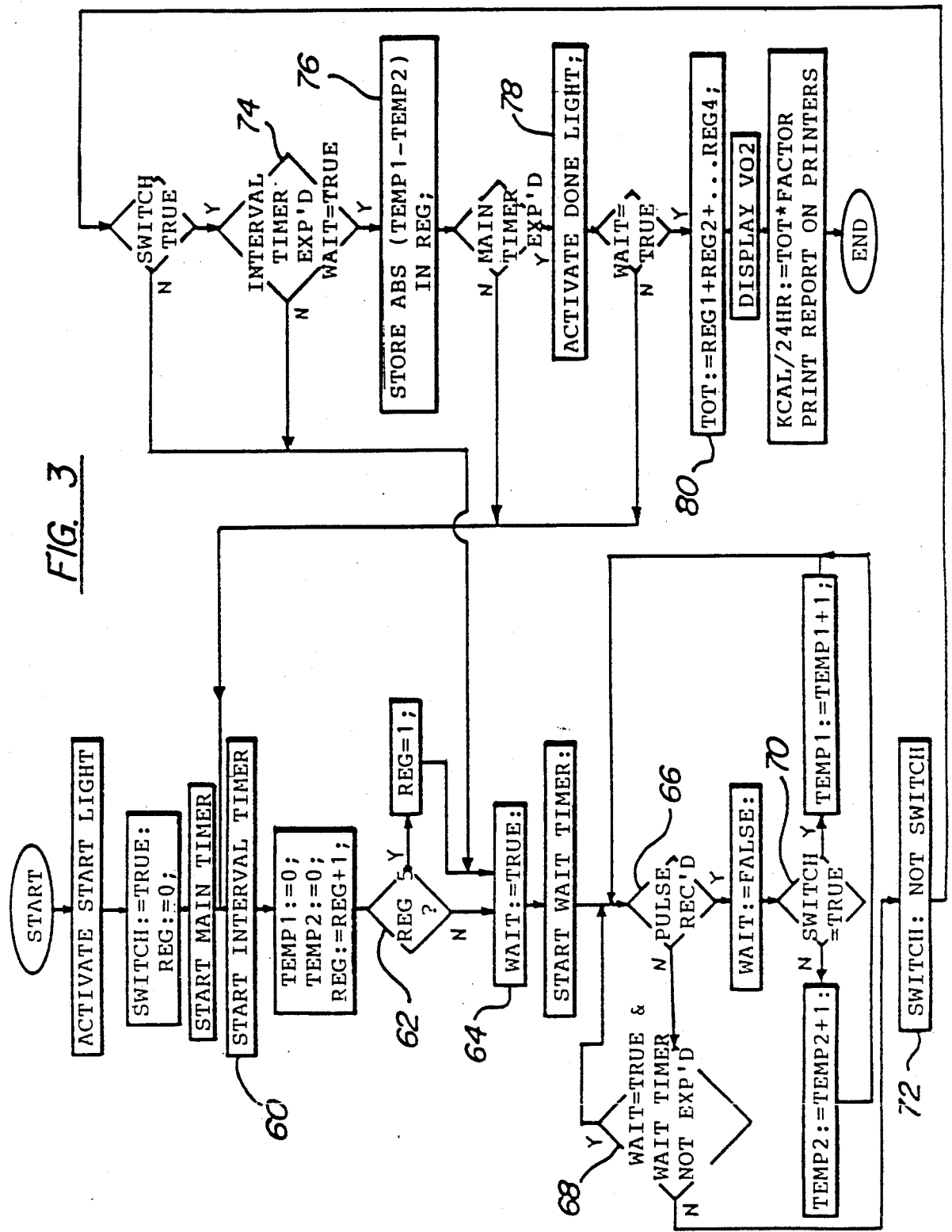
FIG. 3 is a flow diagram illustrating the manner of operation of the microprocessor used with the present invention.

FIG. 1 illustrates the preferred embodiment of the present invention in use. A user 10 inhales and exhales air from and into a respiratory connector preferably taking the form of a mouthpiece 12 adapted to engage the inner surfaces of the user's mouth so as to form the sole passage for inhaled and exhaled air passing through the mouth. A nose clamp 14 of conventional construction may be employed in connection with the mouthpiece 12 to assure that all respiratory air passes through the mouthpiece. In alternative configurations a mask that engages the nose as well as the mouth might be employed.

The mouthpiece 12 is directly connected to a small instrument housing 18 that is manually held by a handle 19 fixed to the housing. The instrument housing 18 contains the other components of the system and is connected to a microprocesor-based computation and display unit 20. The unit 20 includes an ON/OFF switch 22 and a pair of lED signal lights 24 and 26. The signal light 24 is illuminated when the switch is first thrown to the ON position to indicate that the test is underway. At the end of a predetermined time, the light 24 is extinguished and the signal light 26 is illuminated, signaling that enough time has elapsed and that the subject may quit at any time. In the preferred embodiment of the present invention, the housing 18 and the mouthpiece 12 are intended for one use and are disposable.

The unit 20 also includes a first digital display 28 which displays the value $VO_2$, the volume of inspired oxygen per minute, and a second display 29 which exhibits the value of Kcal/24 hours, i.e., the value arrived at by multiplying the integral of the difference between the scrubbed inhaled volume and the scrubbed exhaled volume by a constant.

FIG. 2 provides a schematic of the circuitry in the instrument housing 18 of the preferred embodiment. The housing includes a carbon dioxide scrubber 30. The scrubber 30 is a container having an inlet and an outlet and a central passageway filled with a carbon dioxide absorbent material such as sodium hydroxide or calcium hydroxide. Such absorbers are well known to the art. Sometimes they include sodium hydroxide and calcium hydroxide admixed with silica in a form known as soda lime. Another absorbent material used is "Baralyme" which comprises a mixture of barium hydroxide and calcium hydroxide.

Preferably the scrubber 30 employs a carbon dioxide absorbent media in the form of a fiber structure in which there is absorbed and retained in liquid a solution of one or more substances capable of chemically binding carbon dioxide, such as aqueous sodium hydroxide solution. An absorber of this type is disclosed in Swedish Patent Application 8502322-4. Such scrubbers are manufactured by ICOR, AB of Bromma, Sweden.

The scrubber 30 becomes saturated with $CO_2$ after some period of use. The preferred embodiment of the present invention uses a small scrubber 30. In an alternative embodiment, the instrument housing 18 of FIG. 1 is of a table top configuration and utilizes a large scrubber 30 that has a longer useful life. In this embodiment, the scrubber is preferably removable from said system so that after becoming saturated, a user may replace it with a new scrubber cartridge. In this table top configuration, the mouthpiece is also removably attached to the system. The microprocessor unit 20 of this embodiment may further include means for keeping track of the number of uses of the scrubber and indicating to the user when it should be replaced.

The circuitry in the instrument housing 18 further includes conduits 32 and 34 connected to the inlet and outlet of the scrubber 30, respectively. The opposite end of the conduit 32 is also connected to two one way valves 36 and 38. One way valve 36 allows the passage of air from the atmosphere into conduit 32. One way valve 38 is connected to one end of another conduit 40 that is directly connected to a mouthpiece 12. The valve 38 allows for air exhaled into the mouthpiece to pass into conduit 32.

Conduit 34 is connected to a flow meter 42, of the turbine type, that measures the volume of air passing through it. Such flow meters are well known in the art. In the preferred embodiment, the flow meter is removably attached to the system so that the housing 18 and the mouthpiece 12 may be disposed of after usage, while the flow meter is retained. An opening in the instrument housing, indicated at 21 in FIG. 1, functions to allow the user to connect and disconnect a flow meter to the system. The flow meter may be calibrated by providing a known volume of oxygen to the system and analyzing the number of pulses generated by the flow meter.

The flow meter 42 is connected to the microprocessor unit 20 via a connection wire 44. The meter 42 provides the microprocesor unit with pulsed signals, each electric pulse representing an increment of flow volume. The microprocessor unit 20 includes a mioroprocessor 39 connected to a display 41 and, in the preferred embodiment, a printer 43. The microprocessor functions to distinguish pulse signals representing inhalations and exhalations by categorizing alternate volume flows, representing inhalations or exhalation together, and to generate integrals of their differences over a period of time. In the preferred embodiment, the microprocessor stores the integrated signals for short periods of time representing increments of use of the calorimeter during the test. At the conclusion of the test, the microprocessor sums the values representing the oxygen consumption over the latter portion of the test, and multiplies this by a constant to arrive at the display of kilocalories/24 hours.

The end of the flow meter 42 opposite the end connected to conduit 34 is connected to two one way valves 46 and 48. Valve 46 allows air passing through the flow meter to exit to the atmosphere. Valve 48 is connected to the other end of the conduit 40 and allows air that has passed through flow meter 42 to enter conduit 40 and exit through the mouthpiece 12. In an alternative embodiment, a flow direction sensor may be disposed between valves 46 and 48 and connected to the microprocessor in order to more accurately distinguish between inhalations and exhalations. Such a sensor may comprise a flap that is normally in a resting position and is moved to two different positions depending on whether air is exiting through valve 46 on an exhale, or passing through valve 48 on an inhale. Two contact sensors are used to sense the position of the flap.

The mouthpiece 12 is directly connected to the conduit 40 and allows a subject to breathe air into and out of the conduit. The system functions as follows: When a user inhales through mouthpiece 12, atmospheric air is drawn into valve 36, through conduit 32, through the scrubber 30, into conduit 34, through the flow meter 42, into valve 48, through conduit 40, to the mouthpiece 12 and into the lungs of the user. Exhaled air passes through the mouthpiece, into conduit 40, through valve 38, into conduit 32, through the scrubber 30 and the flow meter 42, exiting through valve 46 to the atmosphere. The conduits and valves used in the instrument housing 18 are well known to the art and are preferably very short in length in order to minimize the error created by extraneous air in the conduits and valves.

FIG. 3 provides a flow diagram illustrating the general flow of operation of the microprocessor in the preferred embodiment of the present invention. The algorithm uses five registers to store values of integrals of the volumes as generated by the flow meter during five successive intervals.

First, the LED signal light 24 of FIG. 1 is illuminated in order to indicate to the user that the test is underway. The boolean variable SWITCH is then initialized to true and the integer variable REG, for keeping track of the current register in use, is initialized to 0.

Next, the main timer is started. This timer expires after the minimum time required for the test has past. In the preferred embodiment, this time is 10 minutes.

Next, at the step indicated at 60, an interval timer is started. This timer keeps track of short increments of the total time. In the preferred embodiment this time is 1 minute. The microprocessor finds the integrated difference between the exhaled and inhaled gas volumes for each increment of time. The processor only stores the most recent 5 periods, so that the initial readings that may be inaccurate due to temperature differences between the inhaled and exhaled gas are discarded.

Next, the counter variables VOL1 and VOL2 are initialized to 0, and REG is incremented by one. At 62 it is checked whether the current register is greater than 5. If not, the algorithm goes to the step indicated at 64. If REG>5, then REG is set back to 1 and the algorithm continues at step 64.

At 64, the boolean variable WAIT is set to true. This variable is used to indicate whether the microprocessor is waiting for a pulse signal from the flow meter. Next, a wait timer is started. This timer is used to create a maximum time in which the microprocessor will wait for a pulse signal. Next, the algorithm goes to the step indicated at 66.

At 66, it is checked whether a pulse signal has been received from the flow meter. If not, the algorithm goes to the step indicated at 68. If a pulse has been received at 66, WAIT is set to false and at step 70 it is checked whether SWITCH is true. If it is, VOL1 is incremented. If it is not, VOL2 is incremented. In either case, the algorithm then goes back to step 66. In the alternative embodiment utilizing the flow direction sensor, no SWITCH variable is needed for the algorithm. In this embodiment the microprocessor may check the signal being received from the flow direction sensor and then increment VOL1 if the user is inhaling or VOL2 if he is exhaling.

At 68, it is checked whether both WAIT is true and the wait timer has not expired. If either of these conditions are not true, the algorithm goes to the step indicated at 72. Else, the algorithm continues at step 66.

At 72, SWITCH is complemented. Next, it is checked whether SWITCH is set to true. If so, the algorithm goes to the step indicated at 74. If SWITCH is false, the algorithm goes back to step 64.

At 74, it is checked whether either the interval timer has expired or WAIT is set to true. IF either of these conditions is true, the algorithm continues to the step indicated at 76. Else, it goes back to step 64.

At 76, the absolute value of the difference between VOL1 and VOL2 ( the difference between exhaled and inhaled oxygen volumes ) is stored in the current register. Next, it is checked whether the main timer has expired. If so, the algorithm continues to the step indicated at 78. Else, the algorithm goes back to step 60 and goes through the routine another time, loading the integrals of the volume signals for the next interval of time (preferably one minute) into the next register.

At 78, the LED signal light 26 of FIG. 1 is illuminated in order to indicate to the user that he may quit at any time. The microprocessor senses that the user quit when no pulse signal is received from the flow meter for an entire period of the wait timer.

Next, it is checked whether WAIT is set to true. If so, the algorithm continues at the step indicated at 80. IF WAIT is false, the algorithm goes back to step 60.

At 80, the five registers are summed together to arrive at an integral of the difference between exhaled and inhaled oxygen volumes over the latest portions of the test. Next, the volume of the oxygen inspired per minute, $VO_2$, is displayed on the digital display 28 of the microprocessor unit 20, as shown in FIG. 1. Finally, the sum is multiplied by a factor to arrive at the number of kilocalories that the subject expends during a 24 hour period. This factor is arrived at as follows: Approximately 5 kilocalories are expended for every 1 liter of oxygen consumed in a minute. In the preferred embodiment of the present invention, the volumes of oxygen are measured in millimeters. Therefore, the number of kilocalories expended over a 24 hour period=VO$_2$ * 1 liter/1000 ml * 5 kcals/liters/minute * 60 minutes/hour * 24 hours/day. This result is displayed on the digital display 29 of the unit 20, and a report of the test results is outputted to the printer 43, as shown in FIG. 2. An alternative algorithm may also display the volume of oxygen inspired per minute after the main timer has expired and continue to update it after each interval period.

The disclosure of the algorithm depicted in FIG. 3 is not intended to limit the present invention. Many different algorithms may be implemented to achieve the same results. For the purposes of illustration, well-known housekeeping functions, such as error checking features, were omitted from the algorithm of FIG. 3.

FIG. 4 depicts an alternative embodiment of the present invention that includes two flow meters. This embodiment utilizes a carbon dioxide scrubber 90 that is connected at one end to a conduit 92, and at the opposite end to a conduit 94. Conduit 92 is connected to a one way valve 96 at one of its ends. The valve 96 allows air to pass from the atmosphere into conduit 92. The other end of conduit 92 is connected to a flow meter 98. A one way valve 93 is disposed between the conduit 92 2nd the meter 98 that allows air to flow from the conduit to the flow meter. The meter 98 is connected to the microprocessor unit 100 via connection line 102. Air may pass from conduit 92, through flow meter 98, and exit to the atmosphere.

Conduit 94 is connected at one end to a one way valve 104. The opposite ed of valve 104 is connected to a conduit 106. Valve 104 allows for the passage of air from the conduit 106 into the conduit 94. The opposite end of conduit 94 is connected to a flow meter 108. Flow meter 108 is connected to the microprocessor unit 100 via connection line 110. The end of the flow meter 108 opposite the end connected to conduit 94 is connected to a one way valve 112. The valve 112 connects the meter 108 to the end of conduit 106 that is opposite the end connected to valve 104. Valve 112 allows for the passage of air from meter 108 into conduit 106.

Conduit 106 is also directly connected to a mouthpiece, indicated at 114. The mouthpiece is removably attached to the conduit. Furthermore, the scrubber 90 is also removably attached to the system and is preferably a large one of the type that may be used a plurality of times before becoming saturated with carbon dioxide.

The system operates as follows: When a user inhales through mouthpiece 114, atmospheric air is drawn into valve 96, through conduit 92, through the scrubber 90, into conduit 94, through flow meter 108, through valve 112, into conduit 106, through the mouthpiece and into the user,s lungs. Exhaled air passes through the mouthpiece, into conduit 106, through valve 104, into conduit 94, through the scrubber 90, into conduit 92, and through flow meter 98, exiting to the atmosphere.

This embodiment requires calibration of the two flow meters in the manner previously noted and, obviously, a different algorithm for the operation of the microprocessor than the one shown in FIG. 3. In this embodiment, the microprocessor need not distinguish inhalation pulse signals from exhalation signals because it receives two inputs, one for each flow meter. The algorithm may also be further extended to include means for keeping track of the number of times that the installed scrubber is used, and then indicating to the user that the system is due for a new scrubber after a certain limit is passed.

Having thus described my invention, I claim:

1. An indirect calorimeter operative to measure the respiratory oxygen consumption per unit time of a subject, comprising:
    a respiratory connector operative to be supported in contact with the subject so as to pass respiratory gases as the subject breathes into said respiratory connector;
    a scrubber having a gas inlet and a gas outlet and being operative to absorb carbon dioxide from said gases passing between its inlet and outlet;
    flow meter means operatively connected to said respiratory connector and operative to generate signals as a function of the gas volume of said gases passed through such meter means;
    valves and conduits interconnecting said respiratory connector, scrubber, and flow meter means, operative upon the subject inhaling to cause the gas to pass through the scrubber, then through the flow meter means, and then to the subjects respiratory system through the respiratory connector, and upon the subject exhaling to pass the exhaled gas from the respiratory connector first through scrubber, then through the flow meter means; and
    means for receiving the resultant signals from the flow meter means and for generating a signal proportional to the integral of the differences between inhaled and exhaled gas volumes over a period of time.

2. The indirect calorimeter of claim 1 in which said flow meter means comprises a single flow meter connected to the gas outlet of the scrubber by a conduit.

3. The indirect calorimeter of claim 2 wherein said means for receiving resultant signals includes means operative to distinguish the signals generated by said flow meter means that are caused by inhaled gas from signals caused by exhaled gas.

4. The indirect calorimeter of claim 1 wherein said flow meter means comprises an inhaled gas flow meter and and exhaled gas flow meter.

5. The indirect calorimeter of claim 1 in which the gas volume signals produced by both the flow meter means comprise a series of pulses with each pulse representing an increment of gas volume.

6. The indirect calorimeter of claim 1 wherein said flow meter means comprises a turbine operative to operate at rates proportional to the flow of gas through the turbine.

7. The indirect calorimeter of claim 1 wherein said means for receiving the resultant signals from the flow meter means and for generating a signal proportional to the integral of their differences over a period of time includes a microprocessor and a digital display operative to display said signal proportional to the integral of the difference between the signals resulting from inhaled gas and the signals resulting from exhaled gas over a period of time.

8. The indirect calorimeter of claim 7 wherein the microprocessor operates upon its input signals to generate a signal which is a function of the integral of the difference of the input signals over a period of time, multiplied by a constant to produce an output signal which is displayed in units of kilocalories per 24 hours.

9. The indirect calorimeter of claim 7 wherein the microprocessor operates to generate a sequence of signals proportional to the integral of the difference between its two input signals over an increment of time, to store said sequence of signals, and to generate an output signal utilizing the most recently stored portion of said stored signals, whereby the initial signals during the test are not utilized in generating the output signal.

10. The indirect calorimeter of claim 1 wherein the respiratory connector, gas flow meter means, and scrubber are formed in a unitary elongated mechanical structure having the mouthpiece at one end, and including means for manually supporting the structure so that the mouthpiece is in contact with the mouth of the subject.

* * * * *

UNITED STATES PATENT AND TRADEMARK OFFICE
CERTIFICATE OF CORRECTION

PATENT NO. : 4,917,108
DATED : April 17, 1990
INVENTOR(S) : James R. Mault

It is certified that error appears in the above-identified patent and that said Letters Patent is hereby corrected as shown below:

Column 1, line 48, "4,6I9,269" should be --4,619,269--.

Column 3, line 10, "included" should be --includes--.

Column 3, line 59, "IED" should be --LED--.

Column 4, line 69, "mioroprocessor" should be --microprocessor--.

Column 7, line 25, "2nd" should be --and--.

Column 7, line 31, "ed" should be --end--.

Column 7, line 53, "user,s" should be --user's--.

Signed and Sealed this

Twenty-third Day of July, 1991

Attest:

HARRY F. MANBECK, JR.

*Attesting Officer*   *Commissioner of Patents and Trademarks*